United States Patent
May et al.

(10) Patent No.: US 8,523,922 B2
(45) Date of Patent: Sep. 3, 2013

(54) DYNAMIC MULTI-AXIAL FASTENER

(75) Inventors: Jason May, Cordova, TN (US); Joshua Simpson, Collierville, TN (US)

(73) Assignee: Warsaw Orthopedic, Warsaw, IN (US)

( * ) Notice: Subject to any disclaimer, the term of this patent is extended or adjusted under 35 U.S.C. 154(b) by 0 days.

(21) Appl. No.: 13/280,042

(22) Filed: Oct. 24, 2011

(65) Prior Publication Data

US 2013/0103097 A1    Apr. 25, 2013

(51) Int. Cl.
*A61B 17/04* (2006.01)
*A61B 17/86* (2006.01)
*A61F 2/08* (2006.01)

(52) U.S. Cl.
USPC .......................................... 606/305; 606/300

(58) Field of Classification Search
USPC ................... 606/246, 264–278, 300–321
See application file for complete search history.

(56) References Cited

U.S. PATENT DOCUMENTS

| | | | |
|---|---|---|---|
| 7,377,921 B2 | 5/2008 | Studer et al. | |
| 2005/0203516 A1 | 9/2005 | Biedermann et al. | |
| 2006/0084989 A1 | 4/2006 | Dickinson et al. | |
| 2008/0234757 A1 | 9/2008 | Jacofsky et al. | |
| 2009/0005815 A1 | 1/2009 | Ely | |
| 2009/0069849 A1 | 3/2009 | Oh et al. | |
| 2009/0254123 A1 | 10/2009 | Pafford et al. | |
| 2009/0264933 A1 | 10/2009 | Carls et al. | |
| 2009/0281572 A1 | 11/2009 | White | |
| 2010/0030268 A1 | 2/2010 | Flynn et al. | |
| 2010/0030270 A1 | 2/2010 | Winslow et al. | |
| 2010/0030273 A1 | 2/2010 | Mitchell et al. | |
| 2010/0030274 A1 | 2/2010 | Mitchell et al. | |
| 2010/0036422 A1 | 2/2010 | Flynn et al. | |
| 2010/0036426 A1 | 2/2010 | Mitchell et al. | |
| 2010/0036435 A1 | 2/2010 | Winslow et al. | |
| 2010/0036436 A1 | 2/2010 | Winslow et al. | |
| 2010/0036437 A1 | 2/2010 | Mitchell et al. | |
| 2010/0036438 A1 | 2/2010 | Mitchell et al. | |
| 2010/0039275 A1 | 2/2010 | Huang et al. | |
| 2010/0057126 A1 | 3/2010 | Hestad | |
| 2010/0057135 A1 | 3/2010 | Heiges et al. | |
| 2010/0057136 A1 | 3/2010 | Heiges et al. | |
| 2010/0063545 A1 | 3/2010 | Richelsoph | |
| 2010/0063551 A1 | 3/2010 | Richelsoph | |
| 2010/0069962 A1 | 3/2010 | Harms et al. | |
| 2010/0087862 A1 | 4/2010 | Biedermann et al. | |
| 2010/0100137 A1 | 4/2010 | Justis et al. | |
| 2010/0185247 A1 | 7/2010 | Richelsoph | |
| 2011/0046684 A1* | 2/2011 | Abdelgany et al. ........... 606/305 |

\* cited by examiner

*Primary Examiner* — Mary C. Hoffman
*Assistant Examiner* — Christina Negrellirodriguez

(57) ABSTRACT

A device for attaching an elongated member to a vertebral member and provide for dampened movement of the elongated member. The device may include a receiver that receives an elongated member. The receiver may be movably attached to an anchor that may be attached to a vertebral member. A dampener may be positioned within the receiver. Further, one or more slots may be positioned in the receiver. The dampener and/or slots dampen the translational movement of the receiver and attached elongated member relative to the anchor in first and second directions, and may also buffer forces applied into the spine.

20 Claims, 8 Drawing Sheets

DYNAMIC MULTI-AXIAL FASTENER

BACKGROUND

The present application is directed to devices for attaching an elongated member to a vertebral member and, more particularly, to devices that provide for dampened movement of the elongated member.

The spine is divided into a variety of regions including the cervical, thoracic, and lumbar regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebrae that form the sacrum and the coccyx.

Various conditions may lead to damage of the intervertebral discs and the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Elongated members may provide a stable, rigid column that encourages bones to fuse after spinal-fusion surgery. Further, the members may redirect stresses over a wider area away from a damaged or defective region. Also, the members may restore the spine to its proper alignment. In the various surgical procedures, the members may be attached to the exterior of two or more vertebral members, whether it is at a posterior, anterior, or lateral side of the spine.

Proximal Junctional Kyphosis (hereinafter PJK) is a hyperkyphosis of the vertebral segment immediately proximal to a spinal construct. PJK occurs in long spinal constructs, and there are multiple factors that have been hypothesized to play a role in its development. A weakening of the muscles due to muscle dissection, the disruption of the posterior tension band, hybrid constructs (screw/hook), and pre-existing kyphotic hyperflexion have all been reasoned to play a role. Possible side effects of the condition might include facet dislocation and posterior widening of the disc space. Devices should be designed to reduce and/or eliminate PJK.

SUMMARY

The present application is directed to devices to attach an elongated member within a patient. One embodiment includes an anchor having a head and a shaft. The device also includes a receiver attached to the anchor and including a bottom side that faces towards the patient when implanted and an opposing top side. The receiver includes a channel configured to receive the elongated member and an interior space positioned between the channel and the bottom side configured to receive the head of the anchor. One or more slots are positioned between the channel and the bottom side of the receiver. The one or more slots each extend through the receiver and into the interior space and include opposing first and second sides and a closed back side.

At least one of the slots may extend inward from a first end of the receiver and at least one of the slots may extend inward from an opposing second end of the receiver. Slots that extend inward from the first and second ends may be positioned in an overlapping arrangement between the channel and the bottom side of the receiver. At least one of the slots may include a tapered shape. The receiver may include opposing first and second walls that extend along opposing sides of the interior space between the channel and the bottom side, and each of the first and second walls may include at least one slot. A dampener may be positioned within the interior space and may include a receptacle that receives the head of the anchor with the dampener constructed from a more flexible material than the receiver. A threaded fastener may be configured to engage the receiver and apply a downward force on the elongated member to secure the elongated member in the channel, and the head may be positioned away from the channel and isolated from the channel to prevent the force from being applied to the head.

Another device for attaching an elongated member to a patient may include an anchor having a head and an outwardly-extending shaft. A receiver is attached to the anchor and includes a bottom side that faces towards the patient when implanted and an opposing top side, a first end and an opposing second end that face in caudal and cephalad directions when implanted, and opposing first and second sides that extend between the first and second ends. The receiver further includes a channel configured to receive the elongated member and an interior space positioned between the channel and the bottom side, between the first and second ends, and between the first and second sides. The interior space is configured to receive the head of the anchor. One or more slots are positioned in the first side and the second side with each of the slots including opposing first and second sides and a closed back side.

A dampener constructed of a flexible material may be positioned within the interior space, and may include a receptacle to receiver the head of the anchor. The receiver may include a longitudinal axis that extends through the channel and the interior space with a first distance between the longitudinal axis and the first end being different than a second distance between the longitudinal axis and the second end. The dampener may include an elongated shape with a first portion positioned at the first end of the receiver and a second portion positioned at the second end of the receiver. The receptacle may be positioned an unequal distance away from the first and second portions. The first end and the second end may include openings into the interior space and at least one slot may extend inward into the first side from the opening at the first end and at least one slot may extend inward into the second side from the opening at the second end. The slots may be positioned in an overlapping arrangement between the channel and the bottom side of the receiver. Each of the receiver and the dampener may include abutment surfaces that are aligned with a longitudinal axis of the receiver that extends through the channel and the interior space.

Another device may include an anchor having a head and a shaft. A receiver is attached to the anchor and includes a bottom side that faces towards the patient when implanted and an opposing top side. The receiver includes a channel configured to receive the elongated member and an interior space positioned between the channel and the bottom side configured to receive the head of the anchor. Slots are positioned between the channel and the bottom side of the receiver with each of the slots extending into the interior space and including opposing first and second sides and a closed back side. A flexible dampener is positioned in the interior space and around the head of the anchor. The dampener is positioned to be compressed when the receiver moves in one of a first direction and an opposing second direction relative to the anchor.

The dampener may include a bore that extends through the dampener with a first side that faces into the channel and a second side that faces into an opening in the bottom side of the receiver, and the head of the anchor may be positioned in the bore between the first and second sides. The bore may extend through the dampener at a location offset from a center of the dampener. The slots may be positioned in an overlapping arrangement between the channel and the bottom side of the receiver. The receiver may include opposing first and second walls that extend along opposing sides of the interior space between the channel and the bottom side, and each of the first and second walls may include at least one of the slots. A threaded fastener may be configured to engage the receiver and apply a downward force on the elongated member to secure the elongated member in the channel, and the head may be positioned away from the channel and isolated from the channel to prevent the force from being applied to the head.

The various aspects of the various embodiments may be used atone or in any combination, as is desired.

DETAILED DESCRIPTION

Figure 1:
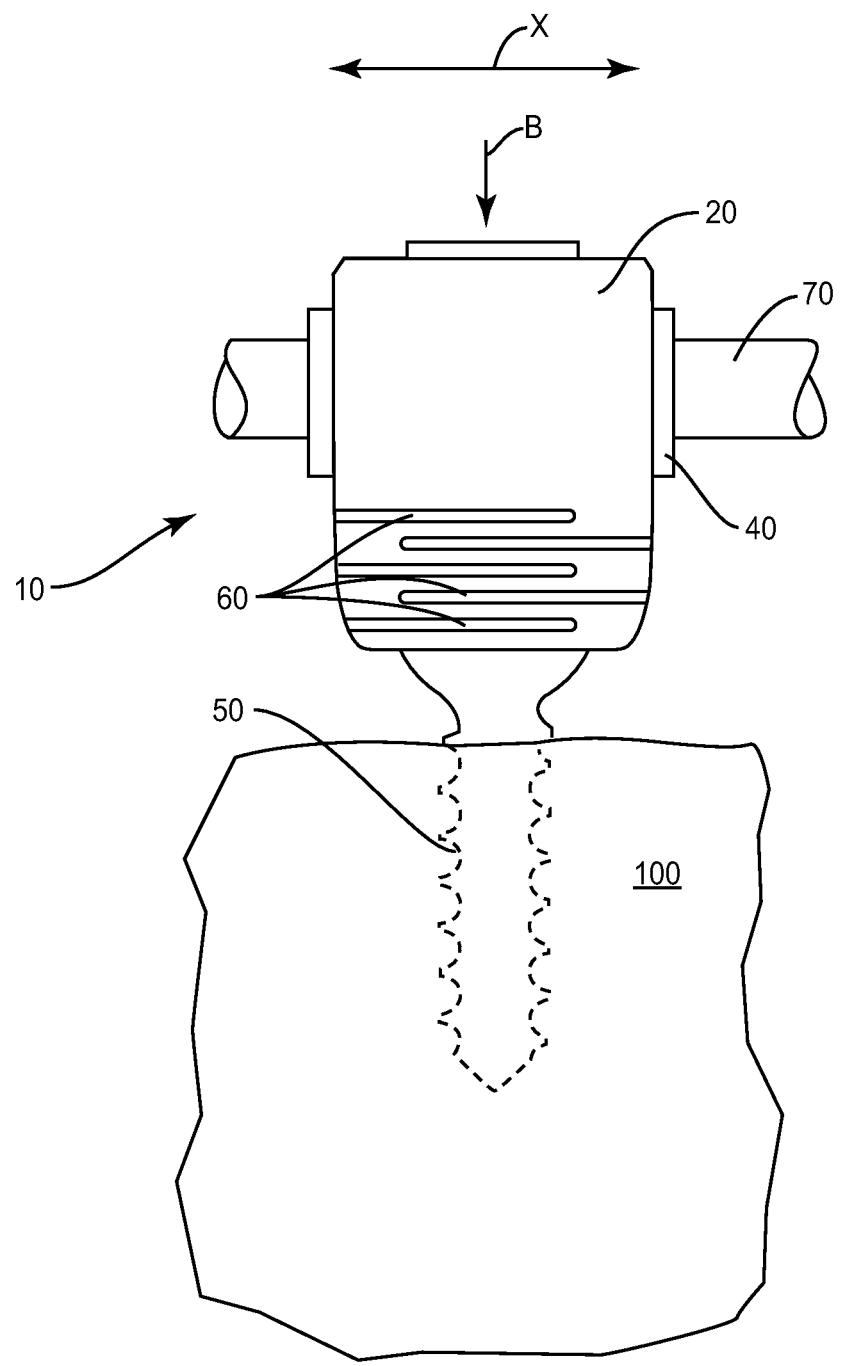
FIG. 1 is a side view of a device that attaches an elongated member to a vertebral member.

The present application is directed to devices for attaching an elongated member to a vertebral member and provide for dampened movement of the elongated member. FIG. 1 schematically illustrates a device 10 for attaching an elongated member 70 to a vertebral member 100. The device 10 includes a receiver 20 that receives the elongated member 70. The receiver 20 is movably attached to an anchor 50 that is attached to a vertebral member 100. A dampener 40 is positioned within the receiver 20. Further, one or more slots 60 are positioned in the receiver 20. The dampener 40 and/or slots 60 dampen the translational movement of the receiver 20 and attached elongated member 70 relative to the anchor 50 in first and second directions indicated by arrow X. These aspects also buffer forces applied into the spine as indicated by arrow B.

Figure 2:
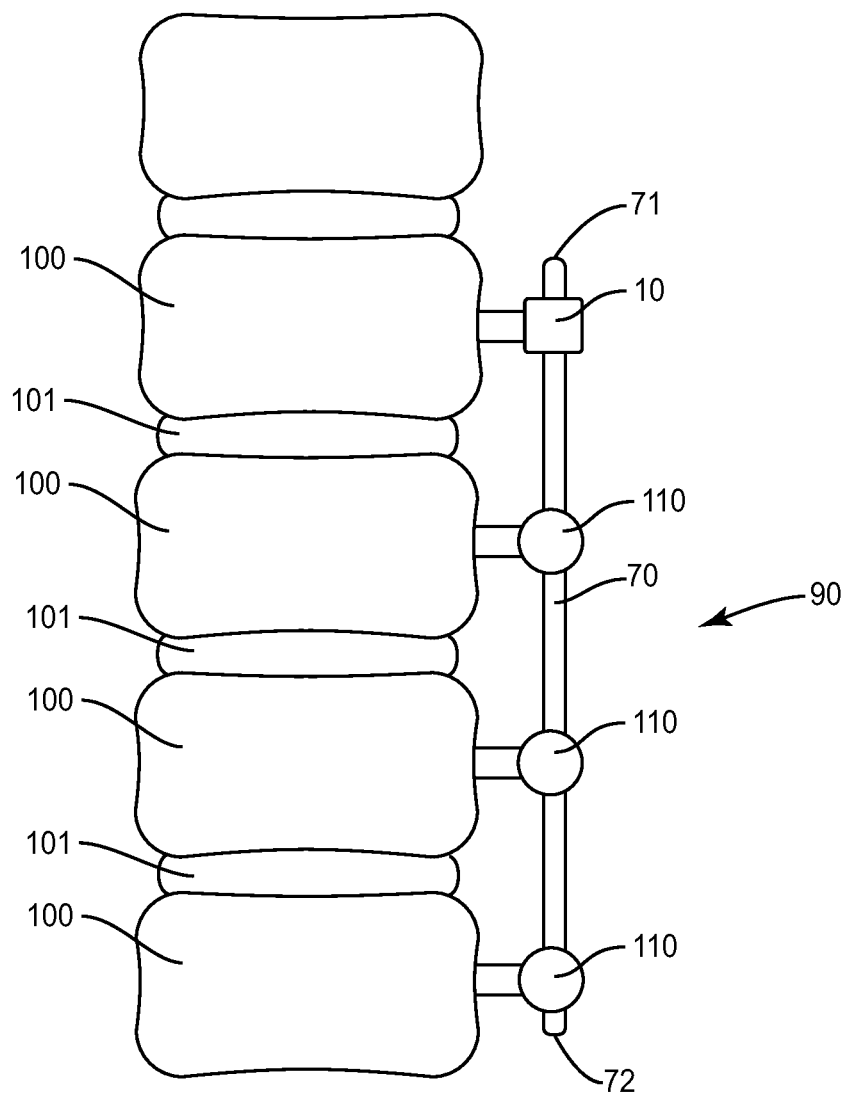
FIG. 2 is a schematic side view of a spinal construct attached to vertebral members.

FIG. 2 illustrates schematically a device 10 used as part of an elongated construct 90 that also includes fasteners 110 and an elongated member 70 that are attached to various vertebral members 100. The elongated member 70 has an elongated shape with a first end 71 facing in a cephalad direction and a second end 72 facing in an opposing caudal direction. The device 10 attaches the elongated member 70 to the vertebral members 100 and provides for dampened translation and rotation in the sagittal plane. In this embodiment, the fastener 10 is positioned at the end 71 of the elongated member 70 facing in the cephalad direction. The fastener 10 may provide for a reduction or elimination of Proximal Junctional Kyphosis (PJK).

Figure 3:
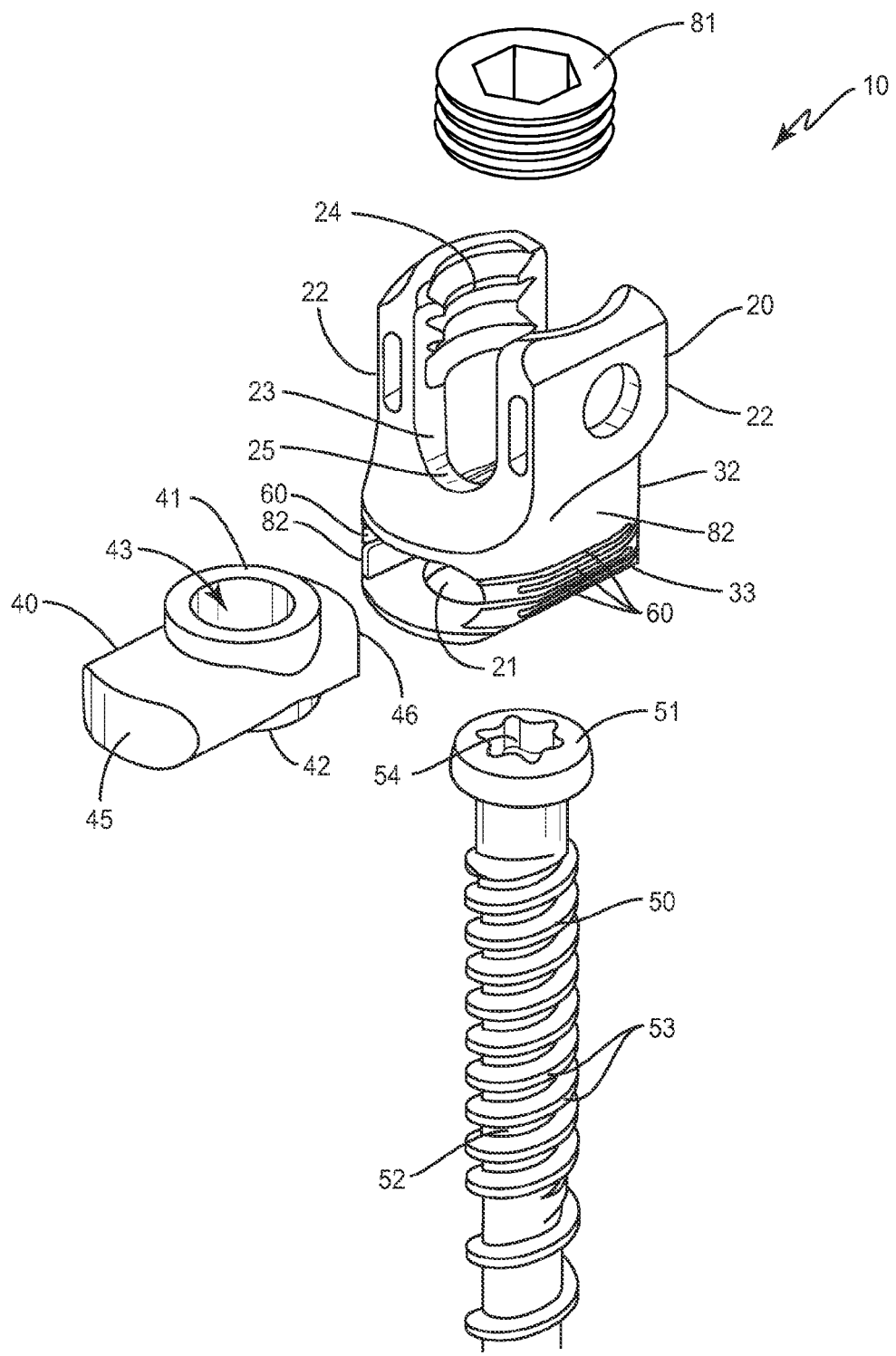
FIG. 3 is an exploded perspective view of a device including a receiver, dampener, fastener, and anchor.
Figure 4:
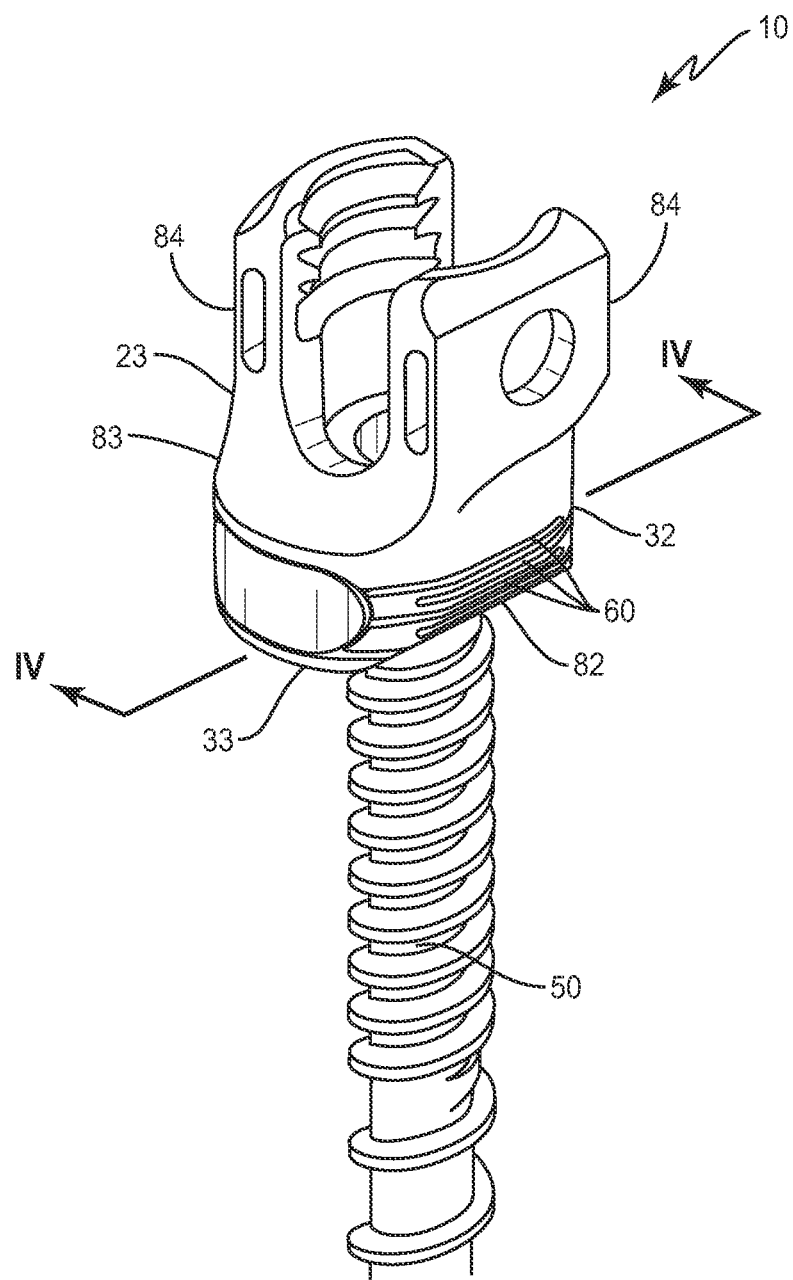
FIG. 4 is a perspective view of a device.
Figure 5:
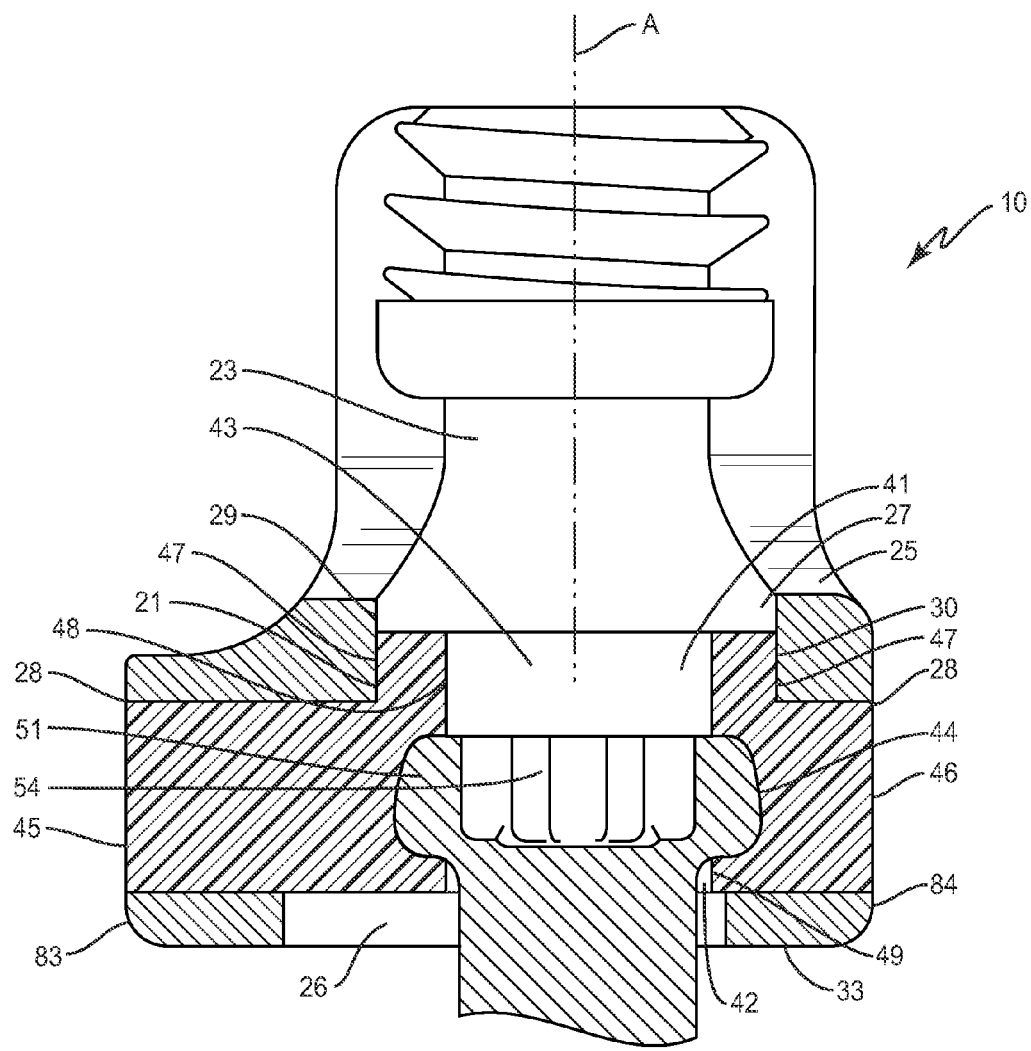
FIG. 5 is a sectional view taken along line IV-IV of FIG. 4.

FIGS. 3, 4 and 5 illustrate embodiments of the fastener 10. The fastener 10 generally includes a receiver 20, a dampener 40, and an anchor 50. These elements work in combination to attach the elongated member 70 to a vertebral member 100. The elements also provides for translation and rotation of the receiver 20 relative to the anchor 50.

The receiver 20 includes arms 22 that are spaced apart and form a channel 23 sized to receive the elongated member 70. The channel 23 includes a bottom wall 25 that may be shaped to conform to the shape of the elongated member 70. The Figures illustrate the bottom wall 25 be arcuate to receive a rod 70 with a circular cross-sectional shape. The bottom wall 25 may also include other shapes to accommodate elongated members 70 of various shapes and sizes.

The channel 23 may be open for the elongated member 70 to be inserted into the channel 23 from the top (i.e., top loading) as illustrated in the Figures, or may be closed at the top and require the elongated member 70 to be inserted into the channel 23 through the side (i.e., side loading). Threads 24 may be positioned towards the upper reaches of the channel 23 to receive a fastener 81 to capture the elongated member 70 within the channel 23. The threads 24 may be positioned on the inner surfaces of the arms 22 to receive a first type of set screw as illustrated in FIG. 3. Other embodiments may include the threads 24 on the outer surfaces of the arms 22 to receive a second type of set screw.

A bottom section 32 of the receiver 20 includes the interior space 21. The bottom section 32 is positioned between the bottom wall 25 of the channel 23 and a bottom side 33 of the receiver 20. The receiver 20 includes a bottom opening 26 that extends through the bottom side 33 and leads into the interior space 21. In one embodiment, the opening 26 is smaller than the anchor head 51 to maintain the anchor head 51 within the interior space 21. In another embodiment, the opening 26 is larger than the anchor head 51. The anchor head 51 is positioned within the dampener 40 which is larger than the opening 26 and maintains the anchor head 51 within the interior space 21.

A top opening 27 may extend between the channel 23 and the interior space 21. The opening 27 is sized to receive a tool that is inserted through the top of the receiver 20 to engage the anchor head 51 to attach the anchor 30 and the receiver 20 to the vertebral member 100. In another embodiment, the receiver 20 is solid between the channel 23 and the interior space 21 (i.e., there is no top opening 27).

The location of the head 51 within the interior space 21 is located away from the channel 23. As illustrated in FIG. 5, the head 51 is located below the bottom wall 25 of the channel 23. This positioning provides for a force applied by the fastener 81 to the elongated member 70 to be isolated from the anchor head 51. This spacing allows for the receiver 20 to move relative to the anchor 50 when the elongated member 70 is secured to the receiver 20.

The interior space 21 is positioned in the bottom section 32 of the receiver 20 between the channel 23 and the bottom side 33. The bottom section 32 includes a pair of opposing sides 82 that are spaced apart about the interior space 21. A first end 83 is located at a first end of the sides 82 and an opposing second end 84 is located at a second end of the sides 82. Openings 28 into the interior space 21 may be positioned at the ends 83, 84. The openings 28 are located between the channel 23 and the bottom side 33.

In one embodiment, the receiver 20 is positioned in the patient with end 83 facing in a cephalad direction and end 84 facing in a caudal direction. The receiver 20 includes a length measured between the first and second ends 83, 84, and a width measured between sides 82. In some embodiments, the receiver 20 includes a greater length and a smaller width. The greater length allows for additional translation along the sagittal plane when the fastener 10 is attached to the vertebral member 100 and the elongated member 70.

Figure 10:
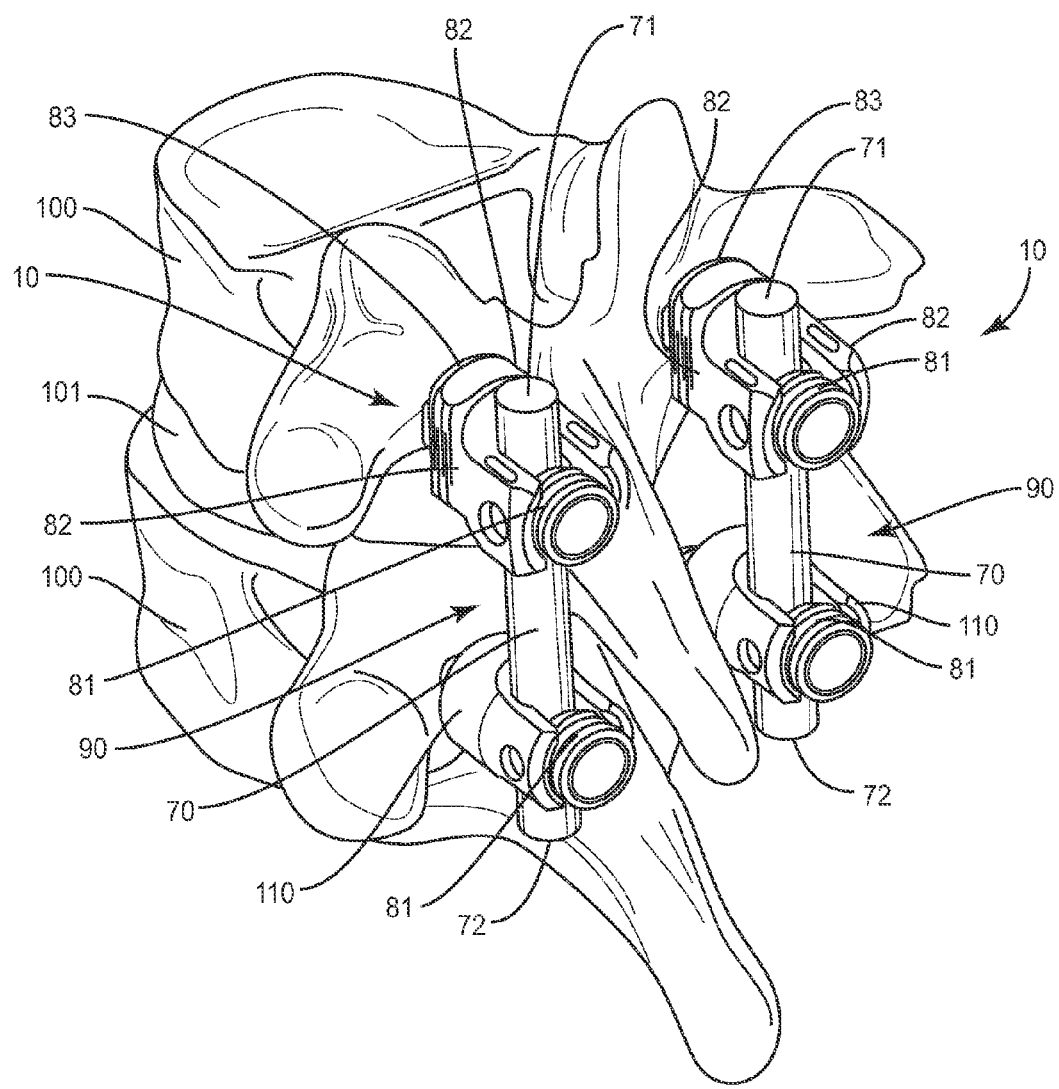
FIG. 10 is a perspective view of a pair of spinal constructs attached to vertebral members.

The receiver 20 may also be configured for one of the ends 83, 84 to be positioned a greater distance away from the longitudinal axis A. In the embodiment best illustrated in FIG. 5, end 83 is positioned a greater distance from the longitudinal axis A than the end 84. This difference in size may provide for additional translational movement in one direction relative to the opposing second direction. In one embodiment, the longer section is oriented in the cephalad direction at the end of the elongated member 70 as illustrated in FIG. 10. This longer section allows for additional translation in the cephalad direction.

The interior space 21 further includes one or more abutment surfaces that contact against the dampener 40 as will be explained in detail below. As best illustrated in FIG. 5, a first abutment surface 29 is positioned at a first side of the top opening 27, and a second abutment surface 30 is positioned at a second side of the top opening 27. The surfaces 29, 30 are elongated along a longitudinal axis A of the receiver 20 that extends through the channel 23 and interior space 21. In one embodiment, each surface 29, 30 is substantially flat and parallel to the axis A. Additional abutment surfaces may also be located in the interior space 21.

One or more slots 60 are positioned in the bottom section 32 between the channel bottom wall 25 and the bottom side 33 of the receiver 20. The slots 60 extend through the sides 82 of the receiver 20 into the interior space 21. As illustrated in FIGS. 3 and 4, the slots 60 extend in the same direction as the channel 23. The slots 34 function to give the receiver 20 flexibility along the longitudinal axis A.

Figure 6:
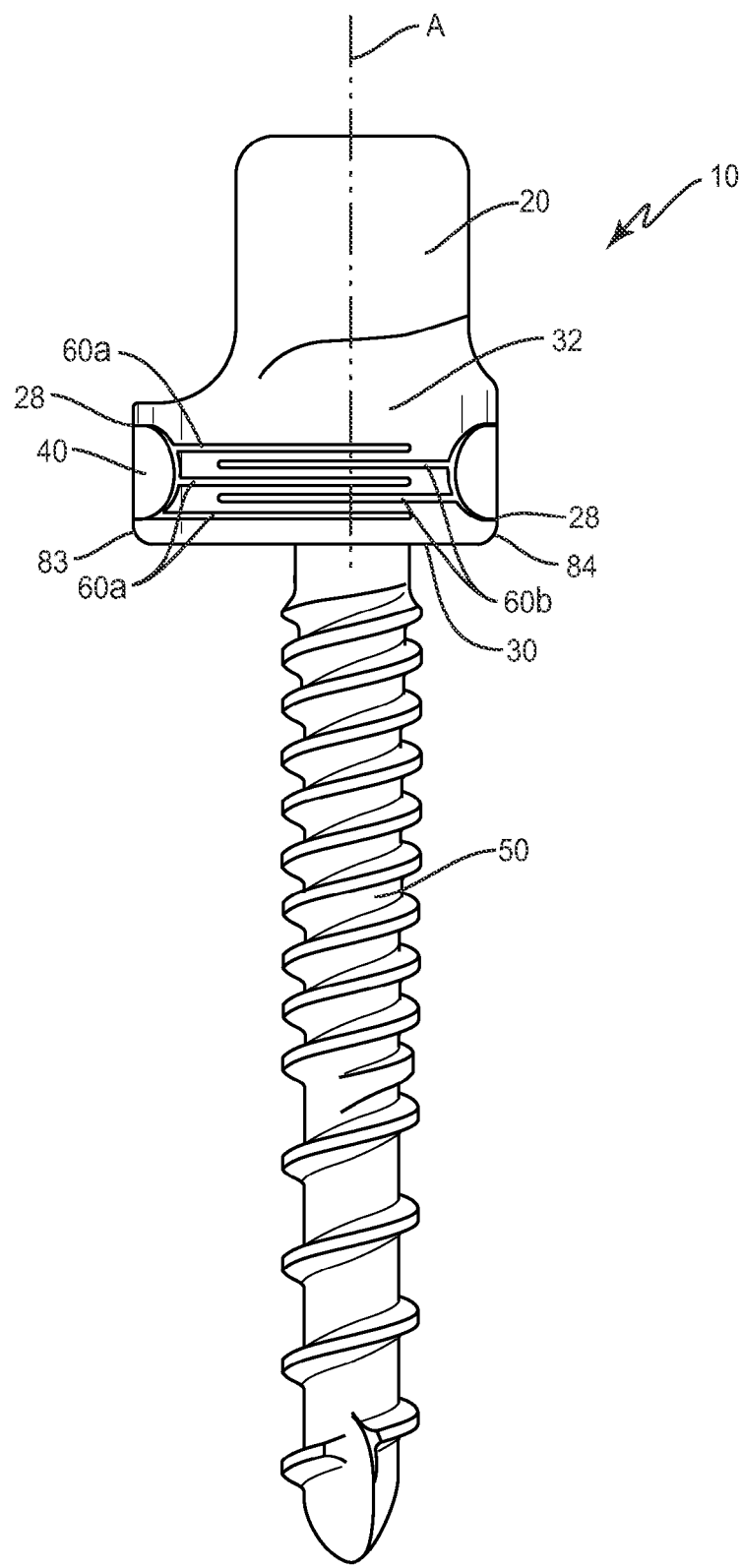
FIG. 6 is a side view of a device.
Figure 7:
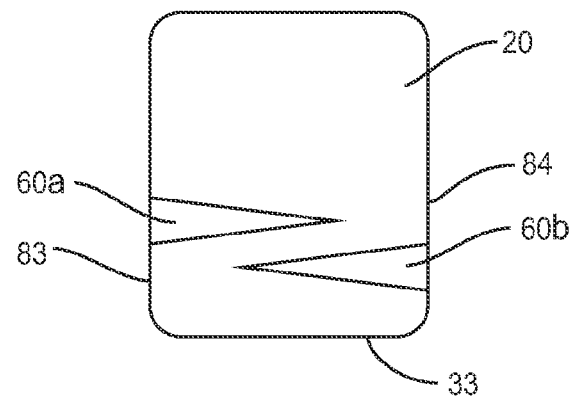
FIG. 7 is a side view of a receiver with slots.
Figure 8:
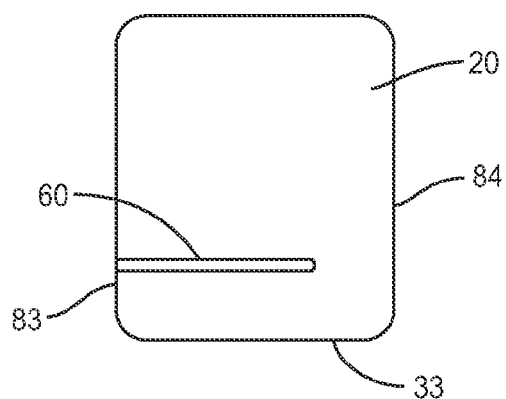
FIG. 8 is a side view of a receiver with a slot.
Figure 9:
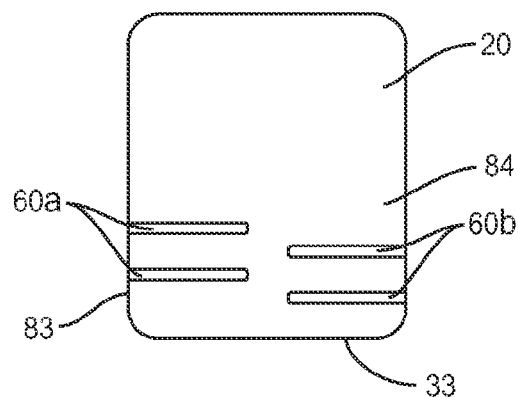
FIG. 9 is a side view of a receiver with slots.

FIG. 6 illustrates one embodiment of a plurality of slots 60 in the bottom section 32 of the receiver 20. The slots 60 extend inward into the bottom section 32 from each of the openings 28. Each slot 60 includes an upper side (i.e., closer to the channel 23) and an opposing tower side (i.e., closer to the bottom side 33). Each slot 60 also includes an inlet at one of the openings 28 and an opposing closed end. The slots 60 include a width measured between the opposing upper and lower sides. FIGS. 6, 8, and 9 each include slots 60 with a substantially constant width. Other embodiments may include slots 60 with different widths. FIG. 7 includes slots 60 with a tapered width that decreases towards the closed end.

In one embodiment, each of the slots 60 extends inward from one end 83, 84. Other embodiments may include slots 60 that extend inward from each of the ends 83, 84. FIGS. 6, 7, and 9 each include first slots 60a extending inward from the first end 83 of the receiver 20, and second slots 60b extending inward from the second end 84 of the receiver 20. In embodiments with slots 60 extending inward from opposing ends 83, 84, the slots 60a, 60b may overlap between the channel 23 and the bottom side 33 as illustrated in FIGS. 6 and 7. Other embodiments may include a non-overlapping arrangement as illustrated in FIG. 9.

The lengths of the slots 60 measured between the inlet and the closed end may vary. Slots 60 may have a length to extend across a majority of the receiver 20 as illustrated in FIGS. 6, 7, and 8. The lengths may also be less as illustrated in FIG. 9. The lengths of each of the slots 60 in a receiver 20 may be the same or may be different.

The slots 60 extend through one of both sides 82 of the receiver 20 and into the interior space 21. In embodiments with slots 60 in both sides 82, 82b as illustrated in FIG. 3, the slots 60 may have the same size, shape, and layout, or may be different.

In some embodiments, the slots 60 are straight between the inlet and the closed end. Other embodiments may include one or more slots 60 that are not straight.

The dampener 40 is positioned in the interior space 21 of the receiver 20 and is configured to receive the anchor 50. The dampener 40 is constructed of a compressible material that allows for translation and rotation of the receiver 20 relative to the anchor 50 when the device 10 is attached to a vertebral member 100 and an elongated member 70.

The dampener 40 may be made of, for example, a pliable polymer, such as, for example, a soft polyurethane composition or a silicone composition. Alternatively, the dampener 40 may be made from a semi-rigid material such as PEEK, flexible polyurethane or polypropylene. Further, the dampener 40 may be made from a rigid material, such as, for example, medical grade stainless steel, titanium, a titanium alloy or other metallic and/or a nonmetallic composition that is formed into a spring. The softer materials provide for more motion of receiver 20 relative to the anchor 50. Similarly, a semi-rigid material would provide a lesser amount of motion of the receiver 20 relative to the anchor 50. A variety of materials applicable for the dampener 40 are disclosed in U.S. Ser. No. 12/253,644 herein incorporated by reference in its entirety. The dampener 40 may be constructed as a single piece, or may be constructed from two or more pieces.

The dampener 40 is positioned in the interior space 21 and may be positioned below the bottom surface 25 of the channel 23. This positioning is best illustrated in FIG. 5 and spaces the dampener 40 away from the elongated member 70 when the member 70 is positioned in the channel 23. This positioning isolates the dampener 40 and the anchor 50 from forces applied by the fastener 81 to the elongated member 70. This spacing and isolation provides for the receiver 20 to move relative to the anchor 50.

The dampener 40 may include a bore 43 that includes a first opening 41 on the top side that faces towards the channel 23 and a second opening 42 that faces in the opposite direction. One or more cut-outs 44 may also extend outward from the bore 43 to accommodate the head 51 of the anchor 50.

The dampener 40 also includes a first end 45 and a second end 46. The first end 45 is positioned at the end 83 of the receiver 20 and the second end 46 is positioned at the opposing end 84. The dampener 40 may be sized to be positioned completely within the interior space 21 of the receiver 20, or may extend outward from the receiver 20 in one or more directions.

The dampener 40 may also include one or more contact surfaces 47 that align with the one or more abutment surfaces 30 in the receiver 20. The contact surfaces 47 may be substantially flat. In one embodiment, the contact surfaces 47 are parallel to the longitudinal axis A when the dampener 40 is positioned in the interior space 21.

The dampener 40 may further be configured to provide for increased translational movement in one direction and limited translational movement in an opposing direction. The dampener 40 may have a greater length measured between a first inner surface 48 of the bore 43 and the first end 45 than between a second inner surface 49 of the bore 43 and the second end 46.

The anchor 50 includes a head 51 and a shaft 52. The head 51 may include a variety of shapes, including but not limited to circular, oval, and flattened as illustrated in FIGS. 2 and 4. The head 51 is sized to fit into the dampener 40 in the interior space 21 of the receiver 20. A receptacle 54 may be positioned on the top of the head 51 opposite from the shaft 52. The receptacle 54 is sized and shaped to receive a tool for mounting the anchor 50. The receptacle 54 is exposed through the bore 43 of the dampener 40 and the channel 23 to receive the tool.

The shaft 52 extends outward from the head 51 and engages with the vertebral member 100. The shaft 52 may include an elongated shape with threads 53 configured to engage with the vertebral member 100. The length and cross-sectional size of the shaft 52 may vary depending upon the context of use. The shaft 52 may have a hook shape to attach to the vertebral member.

The elongated member 70 may be a spinal rod, plate, bar, or other elongated element having a length to extend between at least two vertebral members 100. The elongated member 70 may be solid or hollow along some or all of its length and/or may be of homogenous or heterogeneous composition. The elongated member 70 may be constructed from various materials, including but not limited to stainless steel, titanium, PEEK, and ceramic. The elongated member 70 may be substantially straight, or may be curved along the entire length, or along just a discrete section. The elongated member 70 may include various cross-sectional shapes including but not limited to circular, oval, and polygonal.

FIGS. 2 and 10 illustrate applications of the device 10 in use within a patient to stabilize the spine. The device 10 is part of a spinal construct 90 that also includes fasteners 85 and an elongated member 70.

In use, a surgeon attaches the connectors 85 to vertebral members 70 along a length of the spine. Each of the connectors 85 generally includes an anchor that is attached to a vertebral member 100 and a receiver. The anchor and receiver may be non-movably attached, or may be movably attached with the receiver positionable at a variety of angular positions.

The device 10 is also attached to one of the vertebral members 70. In one embodiment, the device 10 is positioned closest to one of the ends 71, 72 of the elongated member 70. In one embodiment, the device 10 is positioned at the top spinal level of the construct 90.

The device 10 is positioned in the patient with the receiver 20 positioned to accommodate the desired translational movement. In the embodiments of FIGS. 2 and 10, the device 10 is positioned to allow translational movement in the sagittal plane.

The elongated member 70 is attached to each of the fasteners 110 and the device 10. For the device 10, the elongated member 70 is inserted into the channel 23 and the fastener 81 is secured to the receiver 20 to capture the elongated member 70. The fastener 81 also secures the elongated member 70 against the bottom 25 of the channel 23. The anchor head 51 is spaced away from the channel 23 and isolated from the force that is applied through the fastener 81 to the elongated member 70. This spacing and isolation enables the receiver 20 to move relative to the anchor 50.

In one embodiment, the device 10 is positioned in the patient to accommodate translation in the sagittal plane. The device 10 may be positioned with the elongated length of the interior space 21 aligned in the sagittal plane to allow translational movement of the receiver 20 during motion of the spine.

The configuration of the interior space 21 and the dampener 40 dictate the extent of the translational movement. The device 10 may be configured to allow for different amounts of movement in the different directions. In one embodiment, the device 10 is configured to allow for about 3°-4° of extension of the spine. In one embodiment, the device 10 is configured to allow for about 6°-8° of flexion of the spine. This translation movement is dampened in one or both directions by the dampener 40.

In addition to allow for translational movement, the receiver 20 may further be rotatable about the anchor head 51. This may occur as the head 31 rotates within the interior of the dampener 40. The cut-outs 44 and/or bore 43 are sized relative to the anchor head 51 to allow for the rotation.

In one embodiment, the device 10 is positioned at an outer extent of the overall spinal construct 90. FIGS. 2 and 10 illustrates the device 10 placed at the upper extent of the construct 90. This placement and the dynamic ability of the device 10 allows for spinal movement that may reduce or eliminate adjacent segment failure and Proximal Junctional Kyphosis (PJK).

In one embodiment, the device 10 is positioned to accommodate translation movement along the sagittal plane. The device 10 may be positioned in other orientations to accommodate translation in various other planes.

FIGS. 2 and 10 include constructs 90 that include a single device 10. Constructs 90 may also include two or more devices 10. In one embodiment, a construct 90 includes a first device 10 at a first end of the elongated member 70 and a second device 10 at a second end of the elongated member 70. The construct 90 may also include a device 10 positioned at an intermediate section of the elongated member 70.

The device 10 may be positioned at various spinal levels including the cervical, thoracic, and lumbar regions. The device 10 may be used with a variety of constructs 90 used for a variety of spinal treatments including, but is not limited to, treatment of degenerative spondytolisthesis, fracture, dislocation, scoliosis, kyphosis, spinal tumor, and/or a failed previous fusion. The device 10 may also be used in constructs 90 for other applications. Examples include but are not limited to treatment of a patient's long bones (e.g., femur, tibia, fibula, humerus).

In one embodiment, the anchor 50 is top-loaded into the receiver 20. Specifically, the shaft 52 and head 51 are inserted through the top of the receiver 20 and moved downward towards the bottom side 33. The shaft 52 is narrow and fits through the bottom opening 26. The head 51 may be wider than the bottom opening 26, or may be engaged in the dampener 40 to maintain the head 51 in the interior space 21. In another embodiment, the anchor 50 is bottom-loaded into the receiver 20. The head 51 is inserted through the bottom opening 26 in the bottom side 33 and moved into the interior space 21. After this positioning, the bottom opening 26 is reduced to a size smaller than the head 51. The reduction in size may include deforming the walls of the receiver 20 through a turning operation as disclosed in U.S. patent application Ser. No. 12/038,572 which is herein incorporated by reference in its entirety. The reduction may also include securing a member that includes the narrow neck to the receiver 20. In one embodiment, the narrow neck is formed in an annular member that is placed around the anchor shaft 52 and moved over the shaft 52 and to the receiver 20. The annular member is then attached to the receiver 20 using various techniques, such as welding or soldering, or the annular member includes threads that are mated with corresponding threads in the receiver 20.

The receiver 20 may be constructed from various materials, including but not limited to medical grade stainless steel, titanium, a titanium alloy or other metallic alloy.

The device 10 may be implanted within a living patient for the treatment of various spinal disorders and other surgical applications. The device 10 may also be implanted in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device for attaching an elongated member to a patient comprising;
   an anchor having a head and a shaft;
   a receiver attached to the anchor and including a bottom side that faces towards the patient when implanted and an opposing top side, the receiver including a channel configured to receive the elongated member and an interior space positioned between the channel and the bottom side configured to receive the head of the anchor; and
   one or more slots positioned between the channel and the bottom side of the receiver, the one or more slots extending through the receiver and into the interior space and including opposing first and second sides and a closed back side, wherein at least one slot of the one or more slots extends inward from a first end of the receiver and at least one slot of the one or more slots extends inward from an opposing second end of the receiver, the one or more slots that extend inward from the first and second ends are positioned in an overlapping arrangement between the channel and the bottom side of the receiver.

2. The device of claim 1, wherein at least one slot of the one or more slots includes a tapered shape.

3. The device of claim 1, wherein the receiver includes opposing first and second walls that extend along opposing sides of the interior space between the channel and the bottom side, each of the first and second walls includes at least one of the one or more slots.

4. The device of claim 1, further comprising a dampener positioned within the interior space and including a receptacle that receives the head of the anchor, the dampener constructed from a more flexible material than the receiver.

5. The device of claim 4, further comprising a threaded fastener configured to engage the receiver and apply a downward force on the elongated member to secure the elongated member in the channel, the head being positioned away from the channel and isolated from the channel to prevent the force from being applied to the head.

6. A device for attaching an elongated member to a patient comprising;
   an anchor having a head and an outwardly-extending shaft;
   a receiver attached to the anchor and including a bottom side that faces towards the patient when implanted and an opposing top side, a first end and an opposing second end that face in caudal and cephalad directions when implanted, and opposing first and second sides that extend between the first and second ends, the receiver further including a channel configured to receive the elongated member and an interior space positioned between the channel and the bottom side, between the first and second ends, and between the first and second sides, the interior space configured to receive the head of the anchor;
   slots positioned in the receiver with at least one of the slots positioned in the first side and at least one of the slots positioned in the second side, each of the slots including opposing first and second sides and a closed back side; and
   a dampener constructed of a flexible material positioned within the interior space, the dampener including a receptacle to receive the head of the anchor, wherein the receiver includes a longitudinal axis that extends through the channel and the interior space, a first distance between the longitudinal axis and the first end being different than a second distance between the longitudinal axis and the second end.

7. The device of claim 6, wherein the dampener includes an elongated shape with a first portion positioned at the first end of the receiver and a second portion positioned at the second end of the receiver, the receptacle positioned an unequal distance away from the first and second portions.

8. The device of claim 6, wherein the first end and the second end include openings into the interior space, at least one of the slots extends inward from the opening at the first end and at least one of the slots extends inward from the opening at the second end.

9. The device of claim 6, wherein the first side includes at least one of the slots extending inward from the first end and at least one of the slots extending inward from the second end with the slots positioned in an overlapping arrangement between the channel and the bottom side of the receiver.

10. The device of claim 6, wherein each of the receiver and the dampener include abutment surfaces that are aligned with the longitudinal axis of the receiver.

11. A device for attaching an elongated member to a patient comprising:
    an anchor having a head and a shaft;
    a receiver attached to the anchor and including a bottom side that faces towards the patient when implanted and an opposing top side, the receiver including a channel configured to receive the elongated member and an interior space positioned between the channel and the bottom side configured to receive the head of the anchor;
    a plurality of slots positioned between the channel and the bottom side of the receiver, each of the plurality of slots extending into the interior space and including opposing first and second sides and a closed back side; and
    a flexible dampener positioned in the interior space and around the head of the anchor, the dampener positioned to be compressed when the receiver moves in one of a first direction and an opposing second direction relative to the anchor, wherein the dampener includes a bore that extends through the dampener with a first side that faces into the channel and a second side that faces into an opening in the bottom side of the receiver, the head of the anchor positioned in the bore between the first and second sides.

12. The device of claim 11, wherein the bore extends through the dampener at a location offset from a center of the dampener.

13. The device of claim 11, wherein the plurality of slots are positioned in an overlapping arrangement between the channel and the bottom side of the receiver.

14. The device of claim 11, wherein the receiver includes opposing first and second walls that extend along opposing sides of the interior space between the channel and the bottom side, each of the first and second walls includes at least one of the plurality of slots.

15. The device of claim 11, further comprising a threaded fastener configured to engage the receiver and apply a downward force on the elongated member to secure the elongated member in the channel, the head being positioned away from the channel and isolated from the channel to prevent the force from being applied to the head.

16. A device for attaching an elongated member to a patient comprising;
   an anchor having a head and a shaft;
   a receiver attached to the anchor and including a bottom side that faces towards the patient when implanted and an opposing top side, the receiver including a channel configured to receive the elongated member and an interior space positioned between the channel and the bottom side configured to receive the head of the anchor; and
   one or more slots positioned between the channel and the bottom side of the receiver, the one or more slots extending through the receiver and into the interior space and including opposing first and second sides and a closed back side, wherein the receiver includes opposing first and second walls that extend along opposing sides of the interior space between the channel and the bottom side, each of the first and second walls includes at least one of the one or more slots.

17. The device of claim 16, further comprising a dampener positioned within the interior space and including a receptacle that receives the head of the anchor, the dampener constructed from a more flexible material than the receiver.

18. The device of claim 17, further comprising a threaded fastener configured to engage the receiver and apply a downward force on the elongated member to secure the elongated member in the channel, the head being positioned away from the channel and isolated from the channel to prevent the force from being applied to the head.

19. The device of claim 16, wherein at least one slot of the one or more slots includes a tapered shape.

20. The device of claim 16, wherein at least one slot of the one or more slots extends inward from a first end of the receiver and at least one slot of the one or more slots extends inward from an opposing second end of the receiver.

* * * * *